US00PP08618P

United States Patent [19]

Evers

[11] Patent Number: Plant 8,618

[45] Date of Patent: Mar. 1, 1994

[54] HYBRID TEA ROSE PLANT NAMED 'TANRIKAS'

[75] Inventor: Hans Evers, Uetersen, Fed. Rep. of Germany

[73] Assignee: Bear Creek Gardens, Inc., Medford, Oreg.

[21] Appl. No.: 985,880

[22] Filed: Dec. 4, 1992

[51] Int. Cl.[5] ..... A01H 5/00

[52] U.S. Cl. ..... Plt./17

[58] Field of Search ..... Plt. 17, 18

*Primary Examiner*—Howard J. Locker
*Assistant Examiner*—Elizabeth C. Kemmerer
*Attorney, Agent, or Firm*—Klarquist, Sparkman, Campbell, Leigh and Whinston

[57] ABSTRACT

Hybrid Tea rose adapted to greenhouse production on long stems of salmon pink flowers having long vase life, the foliage being dark green, glossy, and disease resistant.

1 Drawing Sheet

1

The present invention relates to a new and distinct variety of rose plant of the Hybrid Tea class which was originated by me by crossing two unnamed seedlings.

The primary objective of this breeding was to produce a new rose variety having long stems, pink blooms, high production and good vase life. The objective was substantially achieved along with other desirable improvements as evidenced by the following unique combination of characteristics which are outstanding in the new variety and which distinguish it from its parents, as well as from all other varieties of which I am aware:

1. Large, clear salmon pink flowers;
2. Long, straight stems;
3. Good cut rose production (175-200 stems per $m^2$ of greenhouse);
4. Excellent vase life;
5. Dark green, glossy, disease-resistant foliage.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—Unnamed seedling.

Classification:

*Botanical.*—*Rosa hybrida.*

*Commercial.*—Hybrid Tea.

FLOWER

Observations made from specimens grown a greenhouse environment in Somis, Calif. from January-June of 1992.

2

Blooming habit: Recurrent.

Bud:

*Size.*—1½" when the petals start to unfurl.

*Form.*—Long, pointed ovoid.

*Color.*—When sepals first divide, bud color is Red Group 38A When half blown, the upper sides of the petals are Red Group 38B; and the lower sides of the petals are Red Group 38B.

*Sepals.*—Color: Green Group 138B. Surface texture: Covered in fine hairs. There are three lightly appendaged sepals. There are two unappendaged sepals with hairy edges.

*Receptacle.*—Color: Green Group 137C. Shape: Apple. Size: Broad, 7/16" wide×¼" long. Surface: Smooth.

*Peduncle.*—Length: Medium, 2¼"-2½". Surface: Prickly. Color: Medium green. Strength: Stiff, erect.

Bloom:

*Size.*—Large. Average open size is 4 inches.

*Borne.*—Singly.

*Stems.*—Long (24-30 inches), strong.

*Form.*—When first open: High centered. Permanence: Retains its form to the end, outer petals curl back.

*Petalage.*—Number of petals under normal conditions: 25-30.

*Color.*—The upper side of the petals is Red Group 38B. The reverse side of the petals is Red Group 38B. The bases of the petals have a greenish white half moon (¼"×¼") at the point of attachment. The major color on the upper side is Red Group 38B.

*Variegations.*—Occasional green streak on the two guard petals.

*Discoloration.*—The general tonality at the end of the first day: No change. At the end of the third day: Slight change in color from Red Group 38A in the bud to Red Group 38B in the open flower.

*Fragrance.*—Slight.

Petals:

*Texture.*—Thick, leathery.

*Shape.*—Round.

*Form.*—Tips slightly recurved, edges slightly quilled.

*Arrangement.*—Imbricated, with a few petaloids in the center.

*Persistence.*—Drops off cleanly.

*Lastingness.*—On the plant: Long, 7 days. As a cut flower: Very long, 10–12 days.

Reproductive parts:

*Anthers.*—Size: Medium. Quantity: Many. Color: Yellow. Arrangement: Regular around the styles.

*Filaments.*—Color: Reddish.

*Pollen.*—Color: Gold yellow. *Styles.*—Color: Reddish.

*Stigmas.*—Color: Greenish white.

Form: Bush.

Growth: Very vigorous, upright and branching.

Foliage:

*Number of leaflets on normal mid-stem leaves.*—5.

*Size.*—Medium, 5"×4".

*Quantity.*—Abundant.

*Color.*—New foliage: Reddish turning green very quickly. Old foliage: Dark green, very glossy.

Leaflets:

*Shape.*—Pointed oval.

*Texture.*—Upper side: Leathery, glossy.

*Edge.*—Serrated.

*Serration.*—Single, small.

*Petiole rachis.*—Color: Green.

*Petiole underside.*—Smooth.

*Stipules.*—Short, bearded.

*Disease resistance.*—Resistant to mildew under normal growing conditions at a greenhouse in Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Medium, hooked downward.

*Color when young.*—Red.

Small prickles:

*Quantity.*—On main stalks: None. On laterals: None.

I claim:

1. A new and distinct variety of rose plant of the Hybrid Tea class, substantially as herein shown and described, characterized particularly as to novelty by the unique combination of its long, straight stems; its good production of cut flowers per $m^2$ of greenhouse; its excellent vase life; its large, clear salmon pink flowers, and its dark green, glossy, disease-resistant foliage.

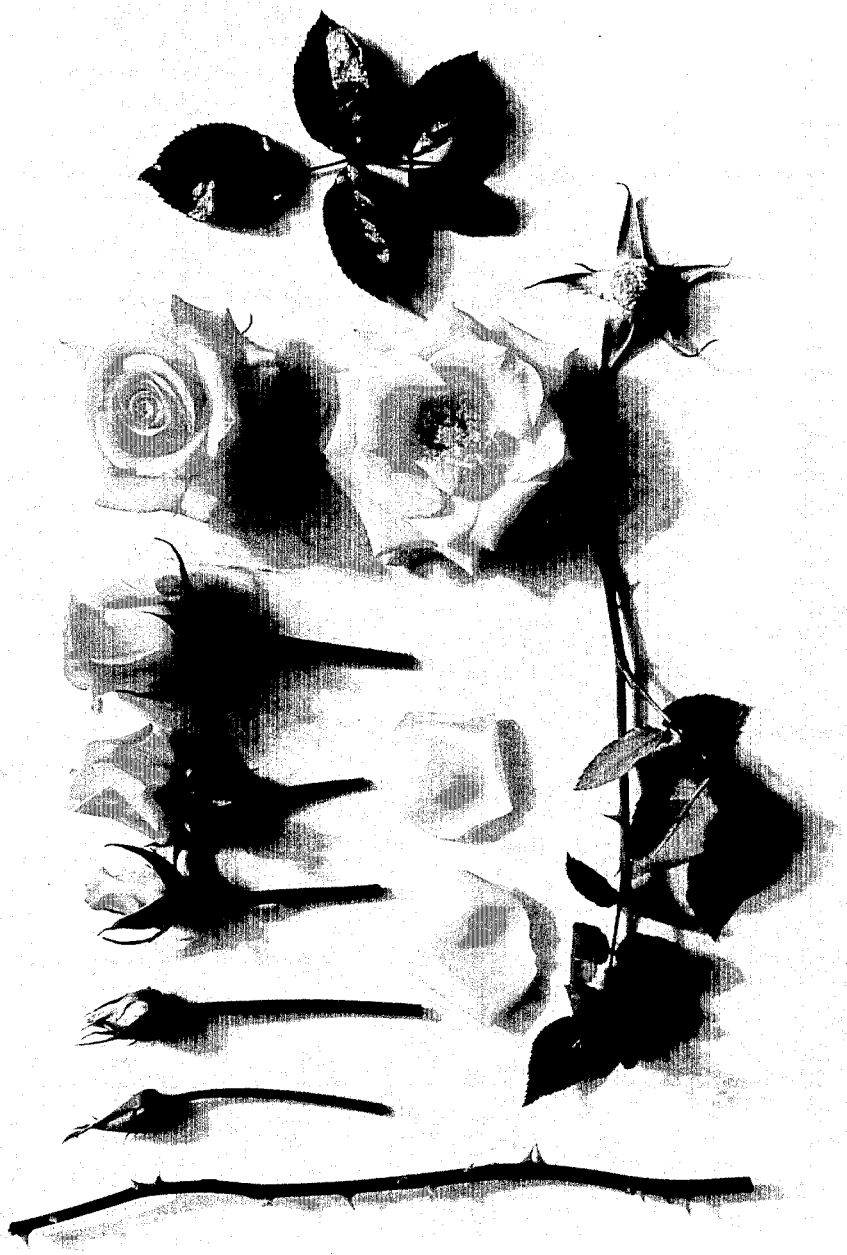

* * * * *